US010019908B2

(12) United States Patent
Imran et al.

(10) Patent No.: US 10,019,908 B2
(45) Date of Patent: *Jul. 10, 2018

(54) SYSTEMS AND METHODS FOR DELIVERING SENSORY INPUT DURING A DREAM STATE

(71) Applicant: InCube Labs, LLC, San Jose, CA (US)

(72) Inventors: Mir Imran, Los Altos Hills, CA (US); Joel M. Harris, Mountain View, CA (US)

(73) Assignee: InCube Labs, LLC, San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/448,335

(22) Filed: Mar. 2, 2017

(65) Prior Publication Data
US 2017/0270810 A1    Sep. 21, 2017

Related U.S. Application Data

(63) Continuation of application No. 14/211,297, filed on Mar. 14, 2014, now Pat. No. 9,620,027.
(Continued)

(51) Int. Cl.
*G09B 5/04* (2006.01)
*A61B 5/04* (2006.01)
(Continued)

(52) U.S. Cl.
CPC .............. *G09B 5/04* (2013.01); *A61B 5/0006* (2013.01); *A61B 5/04001* (2013.01);
(Continued)

(58) Field of Classification Search
CPC ..... G09B 5/04; A61B 5/04001; A61B 5/4812; A61B 5/6814; A61B 5/7405;
(Continued)

(56) References Cited

U.S. PATENT DOCUMENTS 9,620,027 B2    4/2017 Imran et al.
2008/0114263 A1    5/2008 Topp et al.
(Continued)

FOREIGN PATENT DOCUMENTS

EP    1886707    2/2008
WO    9743954    11/1997
(Continued)

OTHER PUBLICATIONS

Lim et al., Analysis of Single-Electrode EEG Rhythms Using MATLAB to Elicit Correlation with Cognitive Stress, International Journal of Computer Theory and Engineering, vol. 7, No. 2, Apr. 2015, pp. 149-155.
(Continued)

*Primary Examiner* — Christine H Matthews
*Assistant Examiner* — Joshua D Lannu
(74) *Attorney, Agent, or Firm* — Kilpatrick Townsend & Stockton LLP

(57) ABSTRACT

Embodiments of the invention provide apparatus, systems and methods for detecting neurological activity indicative of a dream state of a human. Many embodiments of the invention provide apparatus, systems and methods for detecting neurological activity of a human indicative of a dream state or the onset thereof and delivering an input to the user (such as an audio or other sensory input) during the dream state. Particular embodiments of the invention provide systems and methods for detecting neurological activity indicative of the onset or occurrence of a dream state of a human and delivering an audio or other sensory input during the user's dream state. The audio input may be used for learning, delivering messages to the user's subconscious, and/or promoting a state of relaxation.

19 Claims, 5 Drawing Sheets

Related U.S. Application Data

(60) Provisional application No. 61/784,511, filed on Mar. 14, 2013.

(51) Int. Cl.
*A61M 21/00* (2006.01)
*G06F 3/01* (2006.01)
*A61B 5/00* (2006.01)

(52) U.S. Cl.
CPC .......... *A61B 5/4812* (2013.01); *A61B 5/6814* (2013.01); *A61B 5/7405* (2013.01); *A61M 21/00* (2013.01); *G06F 3/015* (2013.01); *A61M 2021/0027* (2013.01); *G06F 2203/011* (2013.01)

(58) Field of Classification Search
CPC ... A61B 5/0006; A61B 5/0476; A61B 5/6803; A61B 5/0482; A61B 5/486; A61B 5/04012; A61B 5/02438; A61M 2021/0027; A61M 21/00; G06F 3/015; G06F 2203/011; H04N 21/42222; H04N 21/42201; A61N 1/36025

See application file for complete search history.

(56) References Cited

U.S. PATENT DOCUMENTS

| | | |
|---|---|---|
| 2008/0306330 A1 | 12/2008 | Lindback et al. |
| 2012/0251989 A1* | 10/2012 | Wetmore .............. A61M 21/00 434/236 |
| 2014/0221779 A1* | 8/2014 | Schoonover .......... A61M 21/02 600/301 |
| 2014/0342338 A1 | 11/2014 | Imran et al. |
| 2014/0343353 A1 | 11/2014 | Imran et al. |

FOREIGN PATENT DOCUMENTS

| | | |
|---|---|---|
| WO | 2012095171 | 7/2012 |
| WO | 2014152887 | 9/2014 |

OTHER PUBLICATIONS

International Application No. PCT/US2014/028122, International Search Report and Written Opinion dated Jul. 17, 2014, 20 pages.

U.S. Appl. No. 14/211,297, Final Office Action dated Aug. 11, 2016, 11 pages.

U.S. Appl. No. 14/211,297, Non-Final Office Action dated Jan. 20, 2016, 15 pages.

U.S. Appl. No. 14/211,297, Notice of Allowance dated Dec. 2, 2016, 9 pages.

* cited by examiner

SYSTEMS AND METHODS FOR DELIVERING SENSORY INPUT DURING A DREAM STATE

RELATED APPLICATIONS

This application is a continuation of U.S. patent application Ser. No. 14/211,297, entitled "Systems and Methods for Delivering Sensory Input During a Dream State", filed Mar. 14, 2014, which claims the benefit of priority to Provisional U.S. patent application Ser. No. 61/784,511, entitled "Systems and Methods for Delivering Sensory Input During a Dream State", filed Mar. 14, 2013; the aforementioned priority application being hereby incorporated by reference for all purposes. This application is also related to U.S. patent application Ser. No. 14/211,692, entitled "Systems and Methods for Delivering Sensory Input During a Dream State", filed Mar. 14, 2014, the full disclosures of which are incorporated herein by reference in their entirety for all purposes.

BACKGROUND OF THE INVENTION

Field of the Invention

Embodiments of the invention relate to systems and methods for detection of neural activity in a user's brain. More specifically, embodiments of the invention relate to systems and methods for detection of neural activity indicative of a dream state of a user. Still more specifically, embodiments of the invention relate to systems and methods for detection of neural activity indicative of a dream state of a user and the delivery of an audio or other sensory input to the user during that dream state.

From Joseph to Sigmund Freud, man has sought to interpret and use his dreams. Authors and artists alike have claimed to be inspired by them. Van Gough said he dreamed his painting, and painted his dream. While Shakespeare said "We are such stuff as dreams are made on and our little life is rounded by a sleep" (The Tempest, IV.i.156-158). However outside of the arts perhaps, no one has succeeded in answering the question of how dreams can be used for one's benefit during waking hours.

A brief discussion will now be presented on sleep and dreams. Throughout the period of sleep, humans typically experience dream periods. Dream periods (e.g., REM sleep state or paradoxical sleep) comprise approximately 15%-20% of the evening's sleep and occur with regularity every 80-100 minutes. While the subject is asleep, however, the body continues to exhibit many characteristic physiological changes. For instance, during sleep there are frequent gross body movements or postural changes. These shifts in position occur with increased frequency before and after dream periods, whereas a period of simulated paralysis occurs during the dream period proper. As a specific example, during human sleep there is a period of increased motor activity before a dream, a period of relative immobility during the dream, and increased motor activity following the dream. This behavior is then repeated 80-100 minutes later. "Ethology of Sleep Studied with Time-Lapse Photography: Postural Immobility and Sleep-Cycle Phase in Humans" by Hobson in Science, Vol. 201, 1978, pp. 1251-1253, includes the analysis of postural changes occurring during sleep and acknowledges the regularity of dreaming but, never has a means for the utilization and calibration of gross body movements in predicting dream occurrences been disclosed. This is also discussed in Advances in Dream Research by Elliot Weitzman, Spectrum Publications, 1976.

In addition to the lack of motor movment, there are are differences between a dream state and a non-dream state. In particular during a dream period, a person's audio centers of the brain are active. Because the user's conscious mind is not active to block sounds heard during this time, it is frequently the case that external sounds heard during a dream state are incorporated into a person's dreams and their subconscious. This lack of conscious filtering, could potentially be beneficial for delivering audio messages to the user for learning, as well as delivering positive messages to a user's subconcious, such as for smoking cessation. What is needed though is a system for detecting when dreams are occurring and delivering desired audio message during that time.

BRIEF SUMMARY OF THE INVENTION

Various embodiments of the invention provide apparatus, systems and methods for detecting neurological activity indicative of a dream state of a human. Many embodiments of the invention provide apparatus, systems and methods for detecting neurological activity indicative of a dream state of a human or the onset thereof and delivering an input to the user such as an audio or other sensory input during the dream state. Particular embodiments of the invention provide apparatus, systems and methods for detecting neurological activity indicative of the onset or occurrence of a dream state of a human (e.g., a REM sleep state) during which time the user's brain is receptive to audio input and delivering an audio input during the user's dream state. The audio input may correspond to spoken words, music or sounds or combinations thereof. The audio input may be used for one or more of learning, delivering a message to the user's subconscious, promoting a state of relaxation or calm or maintaining the user in the REM sleep state (as used herein the word subconscious refers to the user's unconscious mind and/or unconscious mental processes). It may also be used for recording the user's neural-electric brain activity during a dream state, for example, by delivering a specific audio input which results in a particular brain wave or other neural-electric signal which when detected, is then used as a prompt to start recording of the user's neural-electric activity.

The specific content (e.g., music, words, sounds, etc.) comprising the audio input, can be selected by the user, or downloaded from the Internet. It may also be created by an instructor of a particular course (e.g., a language course). In such cases, the content may comprise one or more lectures which the user listens to each night. The lectures can be stored in various media formats including, for example MP3 and WAV format. They also may be stored in various media such as flash drives which may be connected to a port on the system, such as a USB port. In particular embodiments, the content (e.g., a lecture) can be created by an instructor for an on-line course. In such cases, the content can be contained on or at an internet site. The user can then select the content (e.g., a particular lecture) from the site and download it to the audio storage device. Further, the processor or logic resources in the system can include the capability to allow the user to view and select from content files for multiple lectures from a given online course or multiple courses.

In one or more embodiments, depending on the intended purpose (e.g., learning), the content may be customized for the user, by the user, by a person other than the user, or by a computer or combinations thereof. For example, in an application for course learning, the instructor may customize the content for a particular user based upon the user's current proficiency and/or progress in the course. In the case of computer customization, the system may contain a software module (e.g., a customization module) which measures how effectively the user is learning the delivered content after a listening session, and then modifies the content to improve and/or optimize learning. The effectiveness of learning can be determined based on neurological activity measured by the system during or after a content delivery session during an REM sleep state. It may also be based upon a proficiency test in the subject material that the user takes the next day with the results uploaded to the customization module. The modifications in content can include not only the words in the content (e.g., a vocabulary list in a foreign language), but also various characteristics of the content delivery including for example the speed and pitch of the words or other audio signal.

In another aspect of user customization, the customization module can be configured to synchronize and/or modify content delivery based on the users brain waves or other neurological activity. In specific embodiments, the speed of content delivery can be modified based on a characteristic of the user's alpha waves. In one specific embodiment, the speed of content delivery can be correlated to a frequency of the user's alpha waves or other brain wave activity. The correlation may be linear, inverse, first order, second order, etc. Also, in related embodiments, a period of content delivery can be synchronized to a period of brain wave activity, such as an optimal receptivity period as further described below.

In particular embodiments, the system can be configured to detect and determine particular periods (herein referred to as "optimal receptivity periods" or "OR Periods") within a REM sleep state where the user's brain has optimal receptivity to the audio input for learning, etc. and deliver the audio or other sensory input during those periods. Such OR periods may correspond to periods when alpha waves are occurring. The system may include modules operable on the logic resources for detecting the OR period based on detection of alpha waves, or other neurological activity of the user. The OR period can also be preselected to period at the beginning, middle or end of an REM sleep period (e.g., the first two minutes, the middle two minutes or the last two minutes of an REM sleep period. It may also correspond to all or a portion of a particular REM dream period in a sequence of REM dream periods, (e.g., the first, middle or last of a sequence of REM dream periods, and combinations thereof).

In particular embodiments, the system may also be configured to detect such OR periods by looking for changes in the user's brain waves or other neurological activity which occur as a result of the audio (or other sensory input) indicating that the user's brain is hearing or otherwise receptive to the message. In one particular approach for doing this, the system can send out a standard audio message or other sound known to produce changes in the users neurological activity indicative of an OR period (herein defined as an audio ping) and then monitor for such changes. An algorithm for implementing such an approach can be integrated into one or more software modules operable on the logical resource. A variety of such audio pings may be tested for a given user (or class of users) and then have the system determine a subset which has the best correlation (e.g., using various curve fitting or other numerical methods known in the art) to OR periods. This may be done during a learning session where the user listens to range of audio pings. Further in particular embodiments, learning sessions can be customized for the intended purpose of the audio message (e.g., learning, promoting a state of relaxation or delivery of a subconscious message).

Also, the system can be configured to be self-learning such that after each use, the system analyzes particular audio inputs delivered which resulted in an OR period and then modifies (e.g., tunes or fine tunes) the audio ping accordingly in the future. In this way, the system can continuously improve its effectiveness in achieving the desired result in the user, (e.g., promoting learning, relaxation, delivering a subconscious message).

In one embodiment, the invention provides a system for delivering audio content during a dream state comprising wearable electrodes for detecting electrical signals of the brain or head (e.g., the eye area) indicative of a dream state; logic resources for analyzing the electrical signals to determine, for example, when a dream state is occurring; an audio storage device for storing audio signals and an audio output device for delivering an audio signal to the user based on a signal from the logic resources. The system may also include circuitry for processing the electrical signals received from the electrodes.

According to one or more embodiments, the wearable electrodes can be positioned on a headband (also described herein as a head band device) worn by the user during sleep. The electrodes are configured to measure electrical activity of the user's brain or head indicative of a dream state. They can be positioned in various patterns on the headband in order to facilitate detection of brain waves and other neurological activity (e.g., such as that from eye movement) of the user indicative of a dream state such a REM sleep state. Such patterns can include, for example, sinusoidal, vertical or horizontal patterns (all with respect to the horizontal axis of the head band). The spacing in such patterns can be configured based on the particular areas of the head that the electrode(s) is placed, and/or the wavelength of brain wave activity. In one embodiment, the electrodes are attached to the head band in the form of a flexible strip (such as a laminated strip or flex circuit) onto which the electrodes are placed (e.g., by photolithography, etching, etc.). In these and related embodiments, the flexible strip can be configured to bend and flex with movement of the user's head, forehead, etc. such that the electrodes maintain electrical contact with the user's skin during head movement.

According to one more or more embodiments, the electrodes can comprise a variety of surface electrodes known in the art for measuring signals produced by the electrical discharge of neurons in the related areas of the brain or head such as those measured during electroencephalography (EEG), or Electrooculography (EOG) for example. They can be arranged and configured to make electrical contact with any area of the head including areas with and without hair. In particular embodiments, the electrodes can be arranged and configured to make electrical contact with the skin over the forehead and temples so that the user's hair does not interfere with signal detection. The electrodes are operably coupled to a processor or other logic resources. The connection can be via a direct connection or they may be coupled to the electrical circuitry for processing the signals from the electrodes (e.g., for amplification or other purposes) which is, in turn, coupled to the processor.

In various embodiments, other components of the system can also be attached to or otherwise coupled to the headband. This includes the processing circuitry, the processor (or other logic resources), a system power supply (e.g., a battery) and the headphones (or other audio output device used to deliver the audio signal to the user's ears). In some embodiments the headphone or earpiece can have an integral structure with the headband and in other embodiments they may be attached.

In one or embodiments, the system may also include electrical circuitry for processing the electrical signals received from the electrodes. In various embodiments, such processing circuitry can comprise one or more of the amplifier devices such as an op amp and/or pre amp, filter devices such as a low pass, high pass, or band pass filter device, and signal conversion device such as an A/D or D/A device. Still other signal processing circuitry known in the art is contemplated. Further, the processing circuitry can be configured to process the electrical or other signals before or after they are inputted to the processor or other logical resources.

In various embodiments, the logic resources may comprise one or more of a microprocessor, ASIC, analogue device or solid state device. It (they) may be operably coupled to one or more of the processing circuitry, electrodes, audio storage device and audio output device so as to send and/or receive signals from each. It can include one or more algorithms typically in the form of software modules operable on the logic resources for performing various functions. Such functions can include one or more of the following: i) analyzing the electrical signals received from the electrodes; ii) making a determination if the user is in dream state (e.g., REM sleep state); and iii) commencing the delivery of an audio signal to the user. Such functions can also include selecting the particular content of the audio signal (e.g., a lecture in a course), as well modifying and/or customizing the content of the audio signal as is described herein (e.g., modifying content based on the user's brain wave activity, progress in learning, etc.). The functions may also include other system capabilities described herein.

For processor embodiments, the logic resources may include one more integrated devices including for example: i) an A/D converter for converting analog signals received from the electrodes and/or processing circuitry into digital signals; ii) a D/A converter for converting digital signals into analogue signals (e.g., digital signals corresponding to audio content); and iii) a memory device for storing one or more software modules and/or content of the audio delivered to the user. Also, in specific embodiments, the audio storage device can be integrated into the processor.

The audio storage device can include various digital audio storage devices known in the art including various audio storage chips such as those used for various MP3 players. It may also include a flash memory or other connectable memory which the user can plug into a port (such as a USB port) on the system. In various embodiments, as discussed above, the audio storage device may be integral to the logic resources. The audio storage device can also be operably coupled with external devices such as a cell phone or tablet computer and/or the internet so as to receive audio content externally. In alternative embodiments, the audio storage device is external to the system and can be wirelessly coupled to one or more components of the system using radio frequency (RF) or other wireless communication means. According to one such embodiment, the external audio storage device can comprise a cell phone such as an Apple® iPhone™. In a method of using such an embodiment, the user could place the audio by their bed allowing the audio storage device to wireless download selected content to the processor or other component of the system worn by the user. In a related variation, the Apple® iPhone™ or other cell phone device can be configured to be utilized as both the audio storage device and audio output device. In use, such embodiments eliminate the need for the user to wear a headphone earpiece, ear bud, etc., for example Instead, the user need only wear the headband (or other apparatus holding the electrodes) providing for greater comfort during sleep.

The audio output device can comprise a variety of those known in the art. In preferred embodiments the audio output device is configured to be placed in close proximity to the user's ears. In particular preferred embodiments, the audio output device can comprise a headphone device or earpiece. Typically, it will be placed near or over both ears, but may also be positioned over just one ear, for example, in the case of an earpiece. For embodiments of the invention employing a wearable headband or similar structure, it may be attached to the headband or may integral to it. For example, in the case of headphones, the headphones may have an integral structure with the headband. The audio output device may also be removable and/or positionable on headband. In alternative embodiments, the audio output device may comprise a speaker on an external device which is coupled to the system by wire or wirelessly (the latter described above). For wireless embodiments, the speaker may comprise a cell phone or tablet device. In such embodiments, the system and cell phone and/or tablet include communication software (e.g., BlueTooth™) for establishing a handshake between the two devices.

In an exemplary embodiment of a method of using the invention, the user would position the headband or other wearable device on their head prior to sleep. In some embodiments, the system may include a prompt to inform the user that electrodes are properly positioned (e.g., using conductance or resistance measurements). The user may have pre-selected the particular audio content to be played during their dreams or they may do so about the time they put the device on using a plug in audio storage device, such as a flash drive, and/or MP3 player or wireless device such as a cell phone or MP3 player device (e.g. an iPod™ SanDisk Sansa ClipZip™, Creative Zen Stone™). The user then falls asleep. Monitoring of electrical activity indicative of the dream state can begin once sleep commences (which can be determined by use of accelerometers placed on the headband or other wearable embodiments of the system to measure changes in body movement indicative of sleep). Alternatively, it may begin based on an input by the user, such as a button on the headband or signal sent from a wireless device such as cell phone or tablet which is in communication with the system, for example. Detection of the dream state can be done using several approaches or combinations thereof. In one embodiment, detection of the dream state may be done by detecting alpha or similar brain waves of the user. In another approach, the dream state can be detected by saccadic or other movement of the eyes associated with the dream state using electrooculography methods. In yet another approach, detection of the dream state may be achieved by detecting a period of decreased motor activity of the user (as these are characteristic of a dream state) and/or detecting a period of increased motor activity followed by period of decrease motor activity. In such embodiments, motor activity may detected using electrodes placed on the head (e.g., on headband embodiments) as well as other areas of the body. It may also be detected by the use of accelerometers placed on the head (e.g., placed on the headband) or on the other areas of the body (e.g., the hands, arms and legs). In the latter case, the accelerometers can be attached to the user's skin by an adhesive or worn on an arm band and/or leg band device. Also in various embodiments, combinations of the above methods may be used, for example, combining detection of alpha waves with detection of saccadic eye movement, or combining detection of alpha waves with detection of decrease motor activity or even combining detection of alpha wave, saccadic movement and decreased motor activity.

Once the system detects electrical activity indicative of a dream state (e.g., a REM sleep state), it can begin to play the audio content. In some embodiments, it may wait for a period of optimum receptivity (i.e., OR period) which may correspond to all or a portion of the REM sleep state. When the system detects that the user has gone out of a dream state (e.g., REM sleep state), it stops playing the content, but then picks up where it left off, when it detects that the use has re-entered the dream state. In some embodiments, the system may repeat the playing of content from an immediately prior dream period (e.g. 30 seconds, a minute or two or more minutes) to allow the user's brain to be better able to follow the content. Also, in some embodiments, the system can be configured to repeat the same content (e.g., a lecture from a course for learning related embodiments) within the same dream period or over multiple dream periods so as to better reinforce the content in the user's mind and/or subconscious.

To assess the effectiveness of the retention of particular content, the user may take a test immediately upon waking or sometime thereafter, and then may enter the results into the system directly or remotely (e.g., using a wireless device) so that the system can customize one more of the content and its delivery characteristics (e.g., speed, volume and when it is delivered during the dream state) as is described herein. In some embodiments, the user may do a training session where no content is delivered so that the system can collect and interpret electrical signal data from the user's brain so as to be able to determine when the user is an dream state including for example an REM sleep state and/or period of optimum receptivity (i.e., OR periods) as is described herein.

Further details of these and other embodiments and aspects of the invention are described more fully below, with reference to the attached drawing figures.

DETAILED DESCRIPTION OF THE INVENTION

Figure 1A:
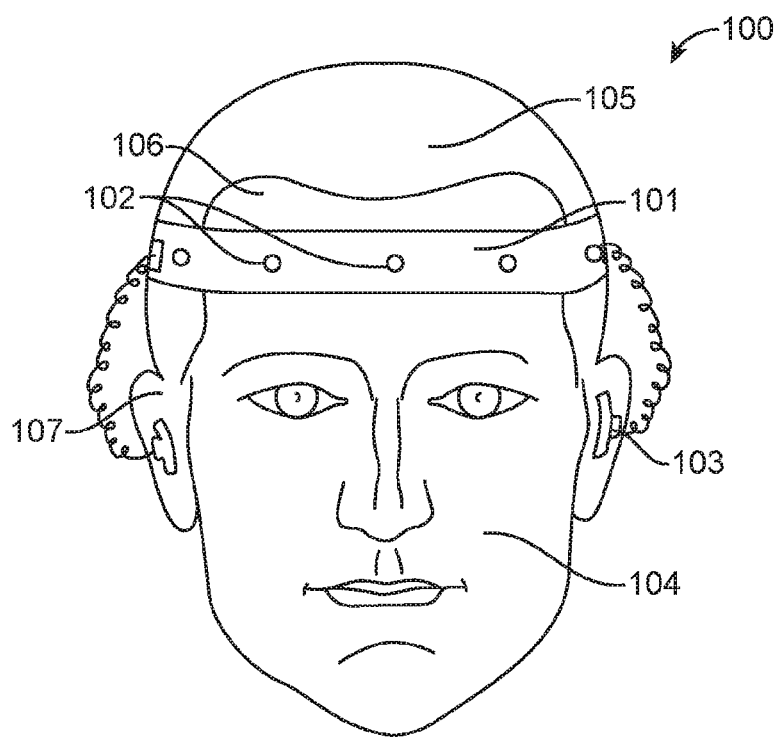
FIG. 1A is a front view of a system for delivering an audio input to a user's brain during a dream state according to an embodiment of the invention.

Various embodiments of the invention provide systems and methods for detecting neurological activity indicative of a dream state of a human. Many embodiments of the invention provide systems and methods for detecting neurological activity indicative of a dream state of a human or the onset thereof and delivering an input to the user such as an audio or other sensory input during the dream state. Particular embodiments of the invention provide systems and methods for detecting neurological activity indicative of the onset or occurrence of a dream state of a human (e.g., REM sleep state) and delivering an audio or other sensory input during the user's dream state. The audio input may correspond to spoken words, music or sounds or combinations thereof. The audio input may be used for one or more of learning, delivering a message to the user's subconscious, promoting a state of relaxation or calm or maintaining the user in the REM sleep state. It may also be used for recording the user's neural activity during a dream state. Other related applications are also contemplated.

Referring to FIGS. 1A, 1B, 1C, 2, 3 and 4, in one or more embodiments, the invention provides a system 100 for delivering audio content during a dream state comprising wearable electrodes 102 for detecting electrical signals 303e of the brain or head indicative of a dream state; logic resources 207 for analyzing the electrical signals to determine, for example, when a dream state is occurring; an audio storage device 206 for storing audio signals and an audio output device 203 for delivering an audio signal to the user based on a signal from the logic resources.

Figure 1B:
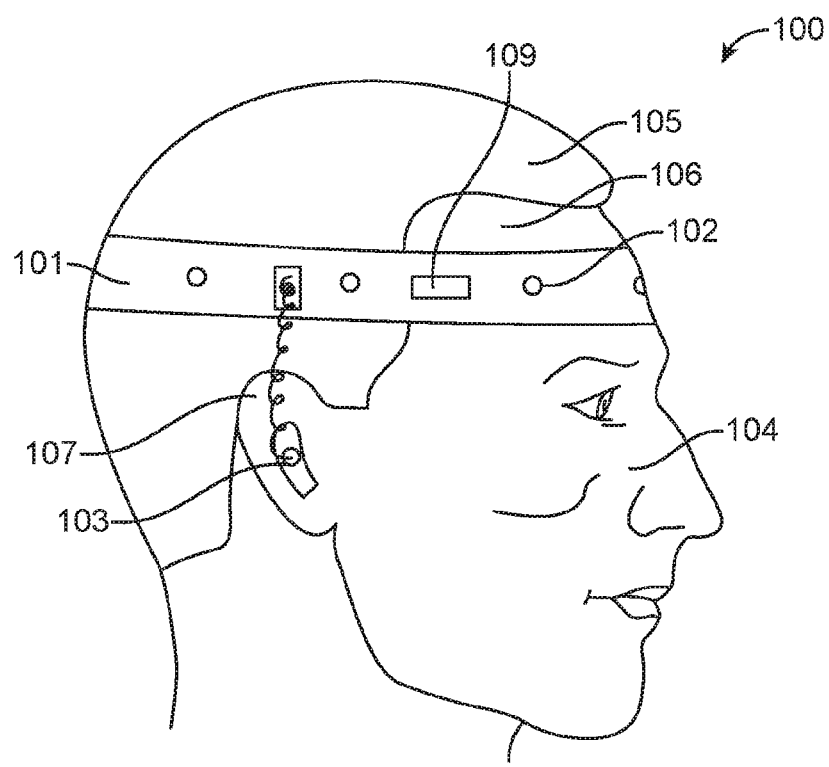
FIG. 1B is a side view of a system for delivering an audio input to a user's brain during a dream state according to the embodiment of FIG. 1A.
Figure 1C:
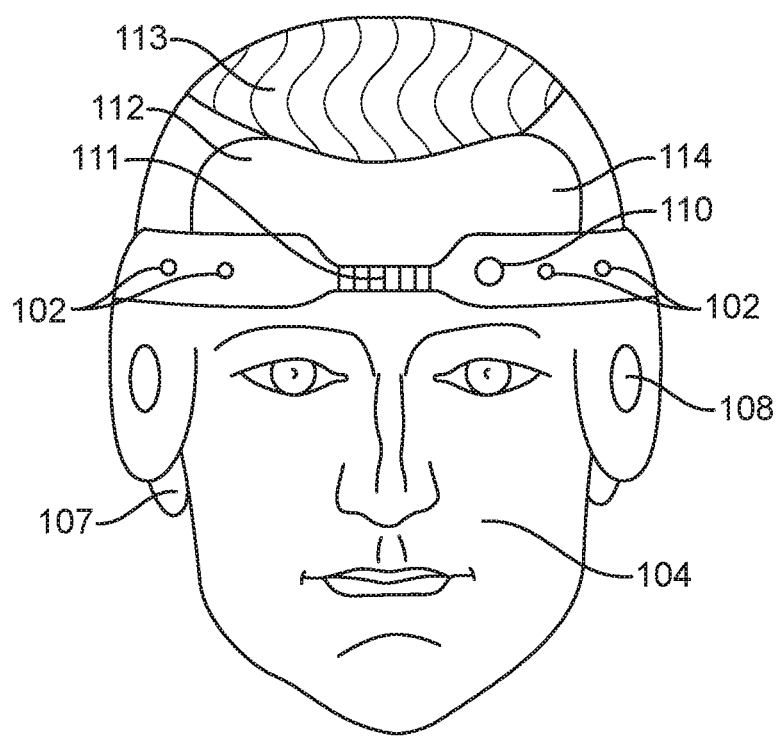
FIG. 1C is a front view of a system for delivering an audio input to a user's brain during a dream state according to an embodiment of the invention.

As shown in FIGS. 1A-1C, and in accordance with one or more embodiments, the wearable electrodes 102 can be positioned on a headband 101 worn (also described herein as a headband device) by the user 104 during sleep. The electrodes 102 are configured to measure electrical activity of the user's brain indicative of a dream state. Typically they will be positioned on an inner surface of the headband so that they can make direct contact with the skin, but also may be positioned on an edge of the headband or on an outside surface. They can be positioned in various patterns on the headband 101 in order to facilitate detection of brain waves and other neurological activity of the user indicative of a dream state such as a REM sleep state. Such patterns can include, for example, sinusoidal, vertical or horizontal patterns (all with respect to the horizontal axis of the headband) as well as combinations thereof. According to one or more embodiments, the spacing in such patterns can be configured based on the particular areas of the head 105 that the electrode 102 are placed, and/or the wavelength of the brain wave activity to be detected such as alpha waves. Alpha waves occur during an REM dream state and have a frequency range from about 7.5 to 12 Hz (with narrower ranges from 7 to 8 Hz, 7.5 to 11.5 Hz, 8 to 12 Hz and 9 to 12 Hz) and an amplitude of about 20 to 200 µV (with a narrower range of 30 to 50 µV). In particular embodiments, the spacing can approximate a multiple of a wavelength of the brainwave activity of the user (e.g., alpha waves). The multiple may correspond to $1\times10{-}8$, $1\times10{-}9$, $2\times10{-}10$, $1\times10{-}10$ or other value. The multiple may be selected so as to tune the electrodes as an antenna, phased array or other receiving device so as to enhance detection by the electrodes of the brain waves (e.g., alpha waves) or other neurological activity indicative of a dream state.

In one or more embodiments, the electrodes 102 can be attached to the headband 101 in the form of a flexible strip (such as a laminated strip or flexible circuit) onto which the electrodes 102 are placed (e.g., by photolithography, etching, etc.) In these and related embodiments, the flexible strip 111 can be configured to bend and flex with movement of the user's head 105, forehead 106, etc. such that the electrodes 102 maintain electrical contact with the user's skin during head movement while asleep. In this way, system 100 allows dream states to be detected throughout the night while the user sleeps.

According to one or more embodiments, the electrodes 102 can comprise a variety of surface electrodes known in the art for measuring signals produced by the electrical discharge of neurons in the related areas of the brain including, for example electroencephalography (EEG). They can be arranged and configured to make electrical contact with any area of the head 105 including areas with 113 and without 114 hair. In particular embodiments, the electrodes 102 can be arranged and configured to make electrical contact with the skin over the forehead 106 and temples so that the user's hair 113 does not interfere with signal detection. They may also be configured to be placed in or around the eye area 115 in order to measure movements of the eye such as saccadic eye movement associated with an REM sleep state using for example, EOG (Electrooculographic/Electrooculography) or other related method for measuring eye movement. The electrodes 102 are operably coupled to a processor 207 or other logic resources 207. The connection can be via a direct connection or they may be coupled to the electrical circuitry 204 for processing the signals 211 from the electrodes 202 (e.g., circuitry for amplification or other purpose) which is, in turn, coupled to the processor 207.

In various embodiments, other components of the system can also be attached to or otherwise coupled to the headband 101. This includes the processing circuitry 204, the processor (or other logic resources) 207, a system power supply (e.g., a battery) 212 and the headphones 108, or earpiece 103 or other audio output device 203 used to deliver the audio signal to the user's ears. In some embodiments, the headphone 108 or earpiece 103 can have an integral structure with the headband 101 and in other embodiments they may be attached.

The specific content (e.g., music, words, sounds, etc.) comprising the audio input, can be selected by the user, or downloaded from the Internet. It may also be created by an instructor of a particular course (e.g., a language course). In such cases, the content may comprise one or more lectures which the user listens to each night. The lectures can be stored in various media formats including, for example MP3 and WAV format. They also may be stored in various media such as flash drives which may be connected to a port on the system, such as a USB port. In particular embodiment, the content (e.g., a lecture or seminar) can be created by an instructor for an on-line course. In such cases, the content can be contained on or at an internet site. The user can then select the content from the site and download it to the audio storage device 206, depicted in FIG. 2. The processor 207 or logic resources 207 in the system 200 can include the capability to allow the user to view and select from content files for multiple lectures from a given online course or multiple courses.

In one or more embodiments, depending on the intended purpose (e.g., learning), the content may be customized for the user. This may be done by the user, by a person other than the user or by a computer. For example, in an application for course learning, the instructor may customize the content for a particular user based upon the user's current proficiency and/or progress in the course. For example, for a language class, the instructor may include a particular list of vocabulary words, or particular phrases and even conversations based on the users progress. For the case of computer customization, the system may contain a software module 208 (e.g., a customization module) which measures how effectively the user is learning the delivered content after a listening session, and then modifies the content to improve and/or optimize learning. The effectiveness of learning can be determined based on neurological activity measured by the system 200 during or after a content delivery session during REM sleep. It may also be based upon a proficiency test in the subject material that the user takes the next day with the results uploaded to the customization module. The modifications in content can include not only the words in the content (e.g., a vocabulary list in a foreign language), but also various characteristics of the content delivery including, for example, the speed and pitch of the words or other audio signal.

In another aspect of user customization, the customization module can be configured to synchronize and/or modify content based on the user's brain waves or other neurological activity. For example, in specific embodiments, the speed of content delivery can be modified based on a characteristic of the user's alpha waves. In one or more specific embodiments, the speed of content delivery can be correlated to a frequency of the user's alpha waves or other brain wave activity. The correlation may be linear, inverse, first order, second order, etc. In a specific case, the speed of content delivery can be increased (e.g. linearly) based on a higher alpha wave frequency (e.g. an increase in the range of 5 to 20%). Further, dynamic adjustments can be made to the speed of content delivery, based on changes in the frequency of the user's alpha wave frequency. In related embodiments, such as shown in FIG. 3, a period of content delivery of the system 300 can be synchronized to a period of brain wave activity, such as an optimal receptivity period (i.e., OR period) during a dream state period 303a, 303b.

Figure 3:
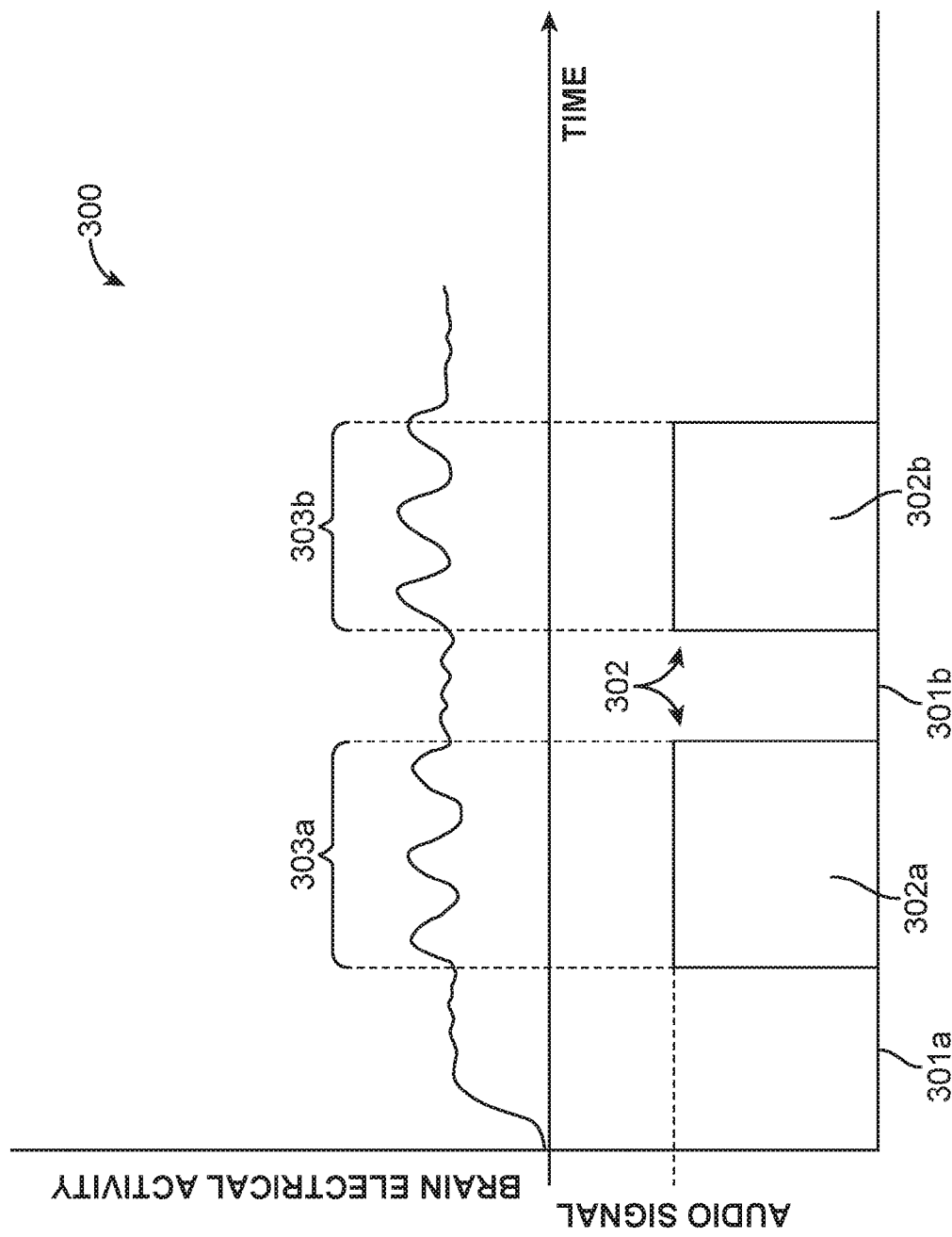
FIG. 3 is a graph illustrating correlation of content delivery to one or more dream state periods of a user according to an embodiment of the invention.

FIG. 3 shows a graph illustrating a correlation of content delivery to one 303a or more 303a, 303b dream state periods of a user. In this particular embodiment, the system 300 can be configured to detect and determine particular periods (herein also referred to as "optimal receptivity periods" or "OR periods") within a REM sleep state (i.e., rapid eye movement sleep state) 303a, 303b period where the user's brain has optimal receptivity to the audio input for activities such as learning and deliver the audio or other sensory input during those periods. Such OR periods may correspond to periods when alpha waves are occurring. The system 200, 300 may include software modules (e.g. module 208) operable on the logic resources 207 for detecting the OR period based on detection of alpha waves, or other neurological activity of the user. In particular embodiments, the systems 200, 300 can be configured to detect an OR period based on one or more of the following: i) a period of frequency and/or amplitude stability of the user's brain waves (i.e. the frequency and/or amplitude are maintained within a selected range); ii) an increase or decrease in frequency of the brain waves; iii) an increase or decrease in amplitude of the alpha brain waves. For the first case, the period of frequency stability may correspond to a frequency range between about 7 to about 13 Hz, with narrower ranges of 7 to 12 Hz, 7.5 to 11.5 Hz, 8 to 12 Hz, 8 to 11 Hz 9 to 12 Hz and 9 to 11 Hz; and the period of amplitude stability may correspond to a range of about 20 to 200 μV with a narrower range of about 30 to 50 μtV. In particularly preferred embodiments, the brain frequency during an OR period may correspond to a range between about 7 to 8 Hz, or 7.25 to 7.75 Hz. The OR period can also be preselected to a period at the beginning, middle or end of an REM sleep period (e.g., the first two minutes, the middle two minutes or the last two minutes of a REM sleep period. It may also correspond to all or a portion of a particular REM dream period in a sequence of REM dream periods, (e.g., the first, middle or last of a sequence of REM dream periods, and combinations thereof).

Figure 4:
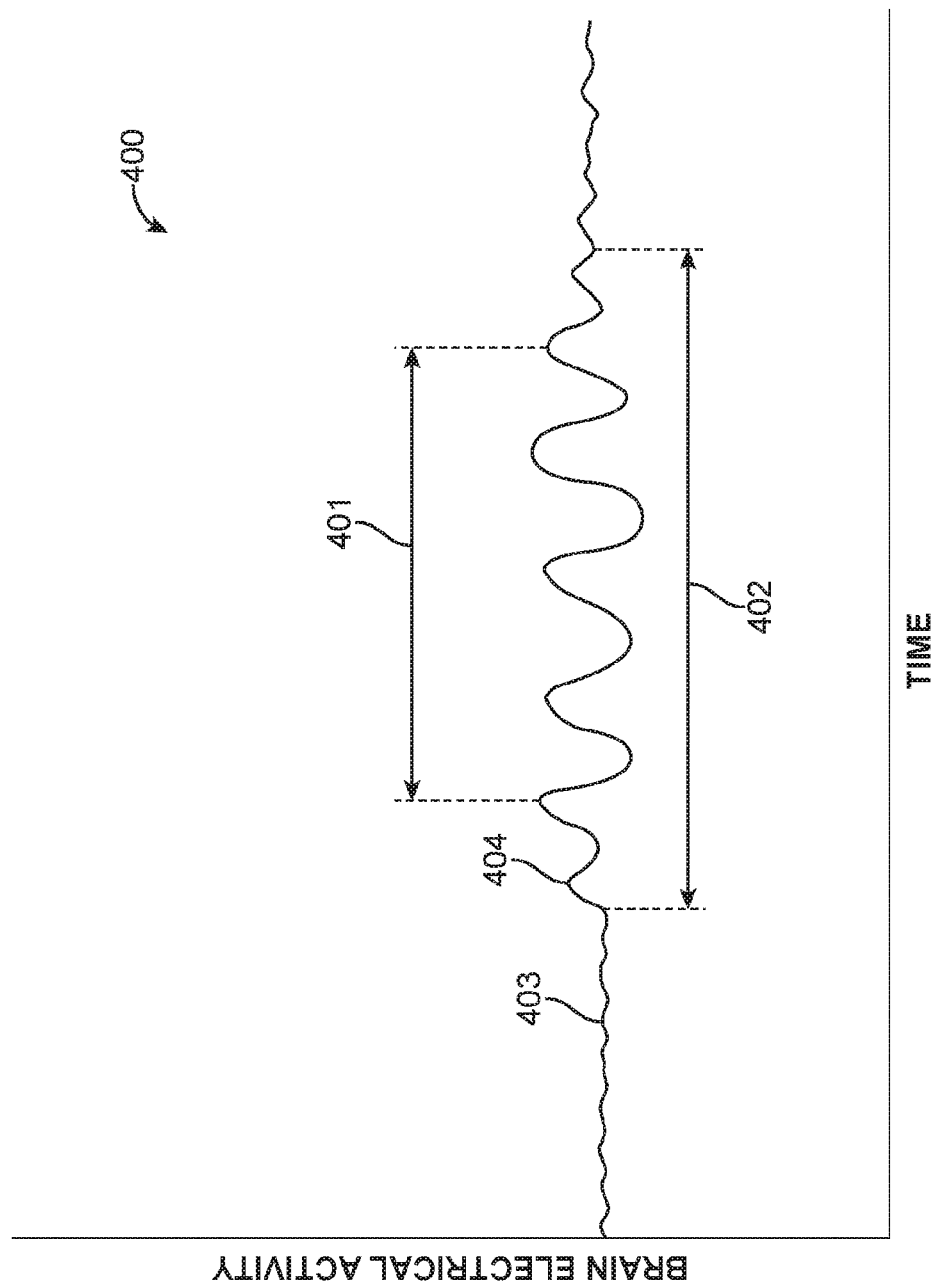
FIG. 4 is a graph illustrating periods of optimal receptivity occurring during a dream period according to an embodiment of the invention.

Further, in particular embodiments, the system 400, shown in FIG. 4, may also be configured to detect such OR periods 401 during an alpha wave/dream state period 402 by looking for changes 404 in the user's brain waves or other neurological activity 403 which occur as a result of the audio (or other sensory input) indicating that the user's brain is hearing the message. In one particular approach for doing this, the system 400 can send out a standard audio message or other sound (herein defined as an audio ping) known to produce changes in the user's neurological activity 403 indicative of an OR period 401 and then monitor for such changes. An algorithm for implementing such an approach can be integrated into one or more software modules operable on the logical resource. A variety of such audio pings may be tested for a given user (or class of users) and then have the system 400 determine a subset which has the best correlation (e.g., using various curve fitting or the numerical methods known in the art (e.g. least squares, cubic spline, fuzzy logic etc.) to OR periods 401 over time. This may be done during a learning session where the user listens to a range of audio pings. Further in particular embodiments, learning sessions can be customized for the intended purpose of the audio message (e.g., learning, promoting a state of relaxation or delivery of a message to the unconscious/subconscious mind, etc.).

Also, the system 400 can be configured to be self-learning such that after each use, the system 400 analyzes particular audio inputs delivered which resulted in an OR period 401 and then modifies (e.g., tunes or fine tunes) the audio ping accordingly in the future. In this way, the system can continuously improve its effectiveness in achieving the desired result for the user (e.g., promoting learning, relaxation, delivering a subconscious message).

Figure 2:
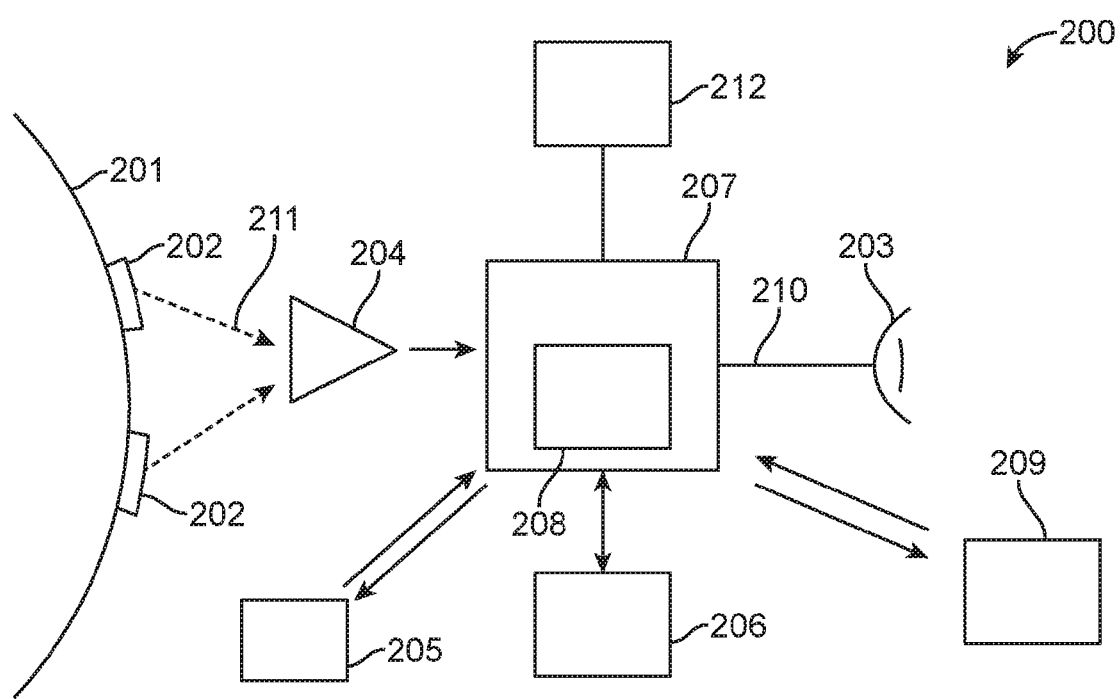
FIG. 2 is a block diagram illustrating various components of an embodiment of a system for delivering a sensory input to the users brain during a dream state according to an embodiment of the invention.

FIG. 2 shows a block diagram illustrating various components of an embodiment of a system 200 for delivering sensory input to the user's brain during a sleep state. In this embodiment, the invention provides a system 200 for delivering audio content during a dream state (as sensed by the electrodes 202 placed against the skin 201 of the user) comprising wearable electrodes 202 for detecting electrical signals of the brain or head indicative of a dream state, logic resources 207 for analyzing the electrical signals to determine, for example, when a dream state is occurring, an audio storage device 205 for storing audio signals and an audio output device 203 for delivering an audio signal to the user based on a signal 210 from the logic resources 207. The system 200 may also include circuitry 204 for processing the electrical signals 211 received from the electrodes 202.

Referring to FIG. 2, the system 200 may also include electrical circuitry 204 for processing the electrical signals 211 received from the electrodes 202. In various embodiments, such processing circuitry 204 can comprise one or more of amplifier devices such as an op amp, pre amp or differential amplifier; filter devices such as a low pass, high pass, or band pass filter device, and signal conversion device such as an A/D or D/A device. Still other signal processing circuitry known in the art is also contemplated. Further, in one or more embodiments, the processing circuitry 204 can be configured to process the electrical or other signals before or after they are inputted to processor or other logical resources 207. Also in various embodiments circuitry 204 can be configured to process a variety of bioelectric signals including one or more of EEG (electroencephalographic) signals as well as EOG (electrooculographaic) signals the later used to detect saccadic or other rapid eye movement associated with a sleep state.

The logic resources 207 may comprise one or more of a microprocessor, ASIC, analogue device or solid state device. It may be operably coupled to one or more of the processing circuitry 204, electrodes 202, audio storage device 206 and/or a remote audio storage device 205 (e.g., cell phone) and audio output device 203 so as to send and/or receive signals from each. It can include one or more algorithms typically, in the form of software modules 208 operable on the logic resources 207 for performing various functions. Such functions can include one or more of the following: i) analyzing the electrical signals received from the electrodes; ii) making a determination if the user is in dream state (e.g., REM sleep state), for example, based on the analysis of the electrical signals received from the electrodes or other inputted signal; and iii) commencing the delivery of an audio signal to the user. Such functions can also include the selection of the particular content of the audio signal (e.g., a lecture in a course), as well modifying and/or customizing the content of the audio signal as is described herein (e.g., modifying content based on the user's brain wave activity, progress in learning, etc.). The functions may also include other system 200 capabilities described herein. In particular embodiments, logic resources 207 or other component of the system 200 can use various pattern matching algorithms known in the art for comparing a pattern or waveform of electrical signals received from electrode 202s (and/or processing circuitry 204) to a pattern, waveform or other characteristic of bioelectric signals (e.g., alpha waves) indicative of a dream state. Further, the pattern or waveform or other characteristic of bioelectric signals indicative of the dream state may be stored in or otherwise operably coupled to logic resources 207 (e.g., by a memory device known in the art).

For processor embodiments, the logic resources may include one more integrated devices including for example: i) an A/D converter for converting signals received from the electrodes and/or processing circuitry into digital signals; ii) a D/A converter for converting digital signals into analogue signals (e.g., digital signals corresponding to audio content); and iii) a memory device for storing one or more software modules and/or content of the audio delivered to the user. In specific embodiments, the audio storage device can be integrated into the processor.

The audio storage device 206 can include various digital audio storage devices known in the art including various audio storage chips such as those used for various MP3 players. It may also include a flash memory or other connectable memory which the user may plug into a port on the system such as a USB port or other connection. In various embodiments, as discussed above the audio storage device 206 may be integral to the logic resources 207. The audio storage device 206 can also be operably coupled with external devices such as a cell phone 205 or tablet computer and/or the internet so as to receive audio content externally. In alternative embodiments, the audio storage device is external to the system 200 and may be wirelessly coupled to one or more components of the system 200 using radio frequency (RF) or other wireless communication means. According to one such embodiment, the external audio storage device can comprise a cell phone 205 such as an Apple® iPhone™. In a method of using such an embodiment, the user could place the audio storage device by their bed allowing the audio storage device to wireless download selected content to the processor 207 or other component of the system 200 worn by the user. In a related variation, the Apple® iPhone™ or other cell phone device can be configured to be utilized as both the audio storage device 205 and audio output device 203. In use, such embodiments eliminate the need for the user to wear a headphone, earpiece 103 or ear bud, for example. Instead, the user 104 need only wear the headband 101 or other apparatus holding the electrodes 102 providing for greater comfort during sleep.

The audio output device 203 can comprise a variety of those known in the art. In preferred embodiments the audio output device is configured to be placed in close proximity to the user's ear(s) 107. Typically, the headphone device will be placed near or over both ears, but may also be positioned over just one ear, for example, particularly in the case of an earpiece. In particular preferred embodiments, the audio output device 203 can comprise a headphone device or earpiece 103. For embodiments of the invention employing a wearable headband 101 or similar structure, it may be attached to the headband 101 or may integral to it. For example, in the case of headphones, the headphones 108 may have an integral structure with the headband 101. The audio output device may also be removable and/or positionable on headband 101. In alternative embodiments, the audio output device 203 may comprise a speaker on an external device which is coupled to the system by wire or wirelessly (the latter described above). For wireless embodiments, the speaker may comprise a cell phone or tablet device. In such embodiments, the system and cell phone and/or tablet can include communication software (e.g., BlueTooth™) for establishing handshake connectivity between two or more devices.

In an exemplary embodiment of a method of using the invention, the user 104 would position the headband 101 or other wearable device on their head prior to sleep. In some embodiments, the system 100, 200 may include a prompt to inform the user that electrodes 102 are properly positioned (e.g., using conductance or resistance measurements). The user 104 may have pre-selected the particular audio content to be played during their dreams or they may do so now using a plug in audio storage device 205 such as a flash drive, and/or MP3 player or wireless device such as a cell phone or MP3 player device (e.g., an iPOD™, SanDisk Sansa Clip Zip™ or Creative Zen Stone™). The user then falls asleep. Monitoring of electrical activity indicative of the dream state can begin once sleep commences (by use of accelerometer(s) 109 placed on headband 101 or other wearable embodiments of the system 100). Alternatively, it may be begin based on an input by the user such as a button 110 on the headband or a signal sent from a wireless device such as cell phone or tablet which is in communication with the system 100, for example.

Detection of the dream state can be done using several approaches and/or combinations thereof. In one embodiment, detection of the dream state may be done by detecting alpha other brain waves of the user which are associated with a dream state. Such brain waves can be detected by analyzing electric signals received from electrodes 102 placed on the head of the user. In another approach, detection of the dream state may be achieved by detecting a period of decreased motor activity of the user (as these are characteristic of a dream state) and/or detecting a period of increased motor activity followed by a period of decreased motor activity. In such embodiments, motor activity may detected using electrodes 102 placed on the head 105 (e.g., on headband embodiments) as well as other areas of the body. It may also be detected by the use of accelerometers 109 placed on the head 105 (e.g., placed on the headband 101) or on the other areas of the body (e.g., the hands, arms and legs) which are configured and placed on the user's body so as to detect movement indicative of motor activity or lack thereof. For areas other than the head, the accelerometers can be attached to the user's skin by an adhesive or worn on and arm band and/or leg band device and can be configured to wirelessly signal processor 207 or other logic resources 207. In some embodiments, inputs from both 102 electrodes (for detecting brain waves associated with sleep) and accelerometers can be used to detect periods of increased or decreased motor activity. In such embodiments, software module 208 can be configured to selectively weigh the inputs from the electrodes and accelerometers so as to make a determination of a dream state. For example, modules 208 may be configured to require both a particular waveform 303w, as well as a minimum level of motor activity as indicated by a threshold level (e.g., a ceiling) signal from the accelerometers so as to make a determination if the user is in a dream state. The module 208 may also be configured to filter out signals from the accelerometers indicative of respiration so that signals do not get used for a determination of motor activity and/or lack thereof.

In yet another approach, a dream state or onset thereof, can be detected by detecting saccadic or other eye movement associated with a dream state. Such eye movement can be detected using EOG methods known in the art and in particular embodiments can be detected from one more electrodes 102 placed in the eye area. An additional or alternative approach for detecting eye movement may include the use of one or more video cameras and the like (which may be placed on headband 101 or other location) that are configured to detect eye movement beneath the closed eyelid. The detection of such eye movement may facilitated by the use of image analysis algorithms incorporated to one or more modules 208 (such modules can be configured to detect small movements and/or displacements of the eyelid caused by saccadic or other eye movement associated with a dream state). In some embodiments, both detected eye movements and brain waves can be used to detect a dream state or onset thereof. In such embodiments, software module 208 can be configured to selectively weigh the inputs from the electrodes used to measure brain waves and eye movements to make a determination of a dream state. For example, modules 208 may be configured to require both a particular waveform 303w, as well as a minimum level or particular type of eye movement so as to make a determination if the user is in a dream state.

In an alternative or additional approach, modules 208 can be configured to determine the occurrence of a dream state or onset thereof from measurement of skin impedance. During sleep, the amount of sweating of the skin can be decreased markedly, as much as three to four time, according to some researchers (J. Narebsk, Human Brain Homeothermy During Sleep And Wakefulness: An Experimental: ACTA NEUROBIOL. EXP. 1985, 45: 63-75; Hbnane, R., et al 1977. Variations in evaporation and body temperatures during sleep in man. J. Appl. Physiol. Respir. Environ Exercise Physiol. 42: 50-55, these papers are incorporated by reference herein in their entirety for all purposes). This results in both an increase in skin impedance due to the decrease sweating and an increase in skin temperature. In one or more embodiments, system 100 can be configured to measure skin impedance using electrodes 102 and skin impedance measurement methods known in the art. The electrodes used for measurement of skin impedance can include those positioned on headband 101 or another location on the body, for example, on the torso, arms or legs. In the latter case, such electrodes can be wirelessly coupled to processor 207 or other logic resources 207. For use of electrodes positioned in the headband 101, the electrodes 102 can be one in the same as those used for measurement of neurological activity of the user's brain or can be separate and specifically configured for skin impedance measurement. For embodiments using skin impedance as an indicator of a dream state, module 208 can be configured to look for a specific increase in skin impedance, for example, a 1, 2, 3 or 4 times increase in skin impedance as the predictor of a dream state (e.g., an REM dream state) or onset thereof. In some embodiments, both skin impedance changes and brain waves can be used to detect a dream state or onset thereof. In such embodiments, software module 208 can be configured to selectively weigh the inputs from the electrodes used to measure brain waves and skin impedance to make a determination of a dream state. For example, modules 208 may be configured to require both a particular waveform 303*w*, as well as a threshold increase in skin impedance (e.g., 1, 2, 3, 4 times etc.) so as to make a determination if the user is in a dream state.

In related embodiments, the dream state or onset thereof can be detected using, temperature sensors 102*t* (e.g., thermisters, thermocouples etc.) placed on the user's forehead or other location on the uses head or body. In the latter case, the temperature sensors can be wirelessly coupled to processor 207 or other logic resources 207. For forehead and head placement, the temperatures sensors 102*t* can be positioned on headband 101. In some embodiments, both skin temperature and skin impedance can be used to detect a dream state (e.g., REM dream state), or onset thereof. In such embodiments, software module 208 can be configured to selectively weigh impedance inputs from electrodes 102 (used as impedance sensors) and temperature sensors 102*t*. Further, a dream state may be determined based on a combination of an increase in skin impedance and skin temperature. In specific embodiments, the module can be configured to determined based on specific increases in skin impedance (e.g., 1, 2, 3, 4 times etc.) and specific increase in skin temperature (e.g., 0.5, 1, 2, 3, 4 degrees Fahrenheit).

With reference to FIG. 3, an explanation will be presented of how and when the system delivers audio content. When the user is a non-dream period, the system is in a non-play period 301, such as non-play period 301*a* before a dream state/period. However, once the system 300 detects a dream state 303*a*, 303*b* (e.g., an REM sleep state), it begins to play an audio content signal 302 during an audio signal play period 302*a*. Detection may be based on analysis of electrical activity 303*e* of the brain or head (e.g., from motion of the eye) or other input such as that from the accelerometers, temperature sensors, etc., indicative of a dream state. In some embodiments, the system may wait for a period of optimum receptivity (i.e., OR period) which may correspond to all or a portion of the REM sleep state 303*a*, 303*b* before the start of content delivery. When the system 300 detects that the user has gone out of a dream state 303*a*, it stops playing the content during a subsequent non-play period 301*b*, but then starts playing during a subsequent period 302*b*, picking up the audio content signal 302 where it left off, when it detects that the use has re-entered the dream state 303*b*. In some embodiments, the system 300 may repeat the playing of content from an immediately prior dream period (e.g., repeating about 30 seconds, a minute or two or more minutes of the prior audio content period) to allow the user's brain to be better able to follow the content. Also, in some embodiments, the system 300 can be configured to repeat the same content (e.g., a lecture from a course for learning related embodiments) within the same dream period 303*a* or over multiple dream periods 303*a*, 303*b* so as to better reinforce the content in the user's mind.

According to one or more embodiments, to assess the effectiveness of retention of the particular content, the user may take a test immediately after waking or sometime thereafter, and then may enter the results into the system directly or remotely (e.g., using a wireless device) so that the system can customize one more of the content and its delivery characteristics (e.g., speed, volume and when it is delivered during the dream state) as is described herein. In some embodiments, the user may do a training session where no content is delivered so that the system can collect and interpret electrical signal data from the user's brain so as to able to determine when the user is an dream state including, for example, a REM sleep state and/or period of optimum receptivity as is described herein. In other embodiments, an OR period may be determined for a given user by delivering content (e.g. a lecture) over selected portions of an REM dream state (e.g. the beginning middle or end) and then administering tests afterwards to determine during which period of the user had the best retention of content.

CONCLUSION

The foregoing description of various embodiments of the invention has been presented for purposes of illustration and description. It is not intended to limit the invention to the precise forms disclosed. Many modifications, variations and refinements will be apparent to practitioners skilled in the art. For example, embodiments of the system can be sized and otherwise adapted for use with children taking into account different head sizes and/or brain wave patterns of children, including those of young children (e.g., toddlers and even infants). Also in various embodiments, the delivery of other sensory input to the user's brain during a dream state is also contemplated (e.g., haptic (feel), visual, taste and smell).

Elements, characteristics, or acts from one embodiment can be readily recombined or substituted with one or more elements, characteristics or acts from other embodiments to form numerous additional embodiments within the scope of the invention. Moreover, elements that are shown or described as being combined with other elements can, in various embodiments, exist as standalone elements. Hence, the scope of the present invention is not limited to the specifics of the described embodiments, but is instead limited solely by the appended claims.

What is claimed is:

1. A method for delivering to an audio input to a user during a dream state, the method comprising:
    detecting, through use of electrodes positioned on the user's head and logic resources operatively coupled to the electrodes, electrical activity of a user's brain indicative of the dream state or the onset of the dream state, wherein the detecting includes detecting a period of optimal receptivity to learning (PORL) from an audio signal to the user during the dream state based on a period of stability of the detected electrical activity, and wherein the logic resources comprise at least one of electrical circuitry or a microprocessor; and
    delivering audio input to the user in response to the detection of the electrical activity indicative of the dream state, wherein the delivered audio input is coordinated with the PORL.

2. The method of claim 1, wherein the period of stability corresponds to a period of stability of the frequency or voltage of the detected electrical activity.

3. The method of claim 1, wherein the audio input comprises spoken words.

4. The method of claim 3, wherein the spoken words contain content used for learning by the user.

5. The method of claim 4, wherein the spoken words comprise a lecture on a subject to be learned by the user.

6. The method of claim 1, wherein the dream state corresponds to a REM sleep state.

7. The method of claim 1, wherein the electrical activity indicative of the dream state comprises alpha brain waves.

8. The method of claim 1, wherein the electrodes are placed in a pattern on the user's head to facilitate detection of electrical activity indicative of the dream state.

9. The method of claim 1, wherein the electrodes are positioned on the user's forehead or face.

10. The method of claim 1, wherein the electrodes are positioned on a headband device worn by the user.

11. The method of claim 10, wherein the detection of the period of optimal receptivity is made based on analysis of sensed electrical activity of the user's brain when a test acoustic output signal is delivered to the user's ears.

12. The method of claim 1, wherein the audio input comprises spoken words, the method further comprising:

detecting electrical activity of the user's brain indicative of a period of optimal receptivity by the user to content contained in the audio input; and wherein the audio input is delivered during the period of optimal receptivity.

13. The method of claim 12, wherein the electrical activity of the user's brain indicative of the period of optimal receptivity comprises alpha brain waves.

14. The method of claim 12, wherein the period of optimal receptivity comprises a portion of a period of a REM sleep state.

15. The method of claim 14, wherein the portion of the period of the REM sleep state comprises the beginning, middle or end of the period.

16. The method of claim 1, wherein the dream state is detected by detecting a period of decreased motor activity of the user.

17. The method of claim 1, wherein the dream state is detected by detecting a period of increased motor activity followed by a period of decreased motor activity.

18. The method of claim 1, wherein a frequency during the period of stability is in a range from 7 to 13 Hz.

19. The method of claim 1, wherein a voltage during the period of stability is in a range from 20 to 200 µV.

* * * * *